United States Patent [19]

Blank et al.

[11] Patent Number: 5,241,099
[45] Date of Patent: Aug. 31, 1993

[54] PROCESS FOR THE PREPARATION OF AMINOMETHYLENE COMPOUNDS

[75] Inventors: Heinz-Ulrich Blank, Odenthal; Helmut Kraus, Cologne, both of Fed. Rep. of Germany

[73] Assignee: Bayer Aktiengesellschaft, Leverkusen, Fed. Rep. of Germany

[21] Appl. No.: 852,275

[22] Filed: Mar. 16, 1992

[30] Foreign Application Priority Data

Mar. 22, 1991 [DE] Fed. Rep. of Germany ....... 4109354

[51] Int. Cl.$^5$ .................... C07B 43/04; C07C 253/30
[52] U.S. Cl. ................... 558/375; 558/251; 558/302; 560/9; 560/22; 560/23; 560/38; 560/41; 560/43; 560/147; 560/156; 560/170; 560/171
[58] Field of Search ................. 558/302, 375, 251; 560/9, 22, 23, 38, 41, 43, 147, 156, 170, 171

[56] References Cited

U.S. PATENT DOCUMENTS 4,620,865 11/1986 Beck et al. ................. 253/30
5,095,133 3/1992 Blank et al. ................. 253/30

FOREIGN PATENT DOCUMENTS 0411417 2/1991 European Pat. Off. .

Primary Examiner—Bernard Dentz
Attorney, Agent, or Firm—Horn Kramer & Woods

[57] ABSTRACT

Aminomethylene compounds of the formula

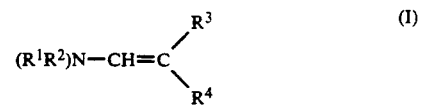

can be prepared by reaction of C-H-acid compounds of the formula

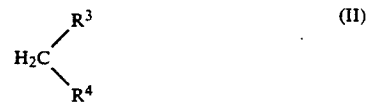

with salts of the formula

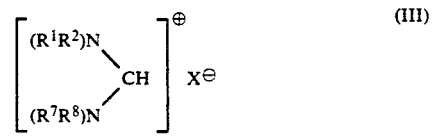

in the presence of simple inorganic bases, where the radicals $R^1$ to $R^4$, $R^7$, $R^8$ and $X^\ominus$ have the meanings given in the description.

13 Claims, No Drawings

PROCESS FOR THE PREPARATION OF AMINOMETHYLENE COMPOUNDS

BACKGROUND OF THE INVENTION

1. Field of the Invention

The invention relates to the preparation of aminomethylene compounds by aminomethylenation of C-H-acid compounds in a single-step reaction.

Aminomethylene compounds, such as aminomethylenated dinitriles, cyanoacetic esters and malonic esters, are important $C_3$ and $C_4$ units in the synthesis of heterocyclic compounds, such as for example derivatives of pyrazole, pyridine and quinoline, which are used as active ingredients for pharmaceuticals and as crop protection agents (U.S. Pat. No. 4,620,865).

2. Description of the Related Art

A number of processes for the aminomethylenation of C-H-acid compounds are known and are listed in German Offenlegungsschrift 39 25 720. This German Offenlegungsschrift itself describes the reaction of C-H-acid compounds with alkoxymethylene-iminium salts or with formamidinium salts, alcoholates being used as the bases required. However, alcoholates are expensive and require elaborate handling because of their reactivity. Furthermore, there is the danger that transesterification reactions may occur when esters are used as the C-H-acid compounds. In DD 257 067, the aminomethylenation of cyanoacetate using the DMF (dimethylformamide)-dimethyl sulphate adduct in the presence of sodium carbonate is described, although yields of only 53–61% of the theoretical yield were achieved.

SUMMARY OF THE INVENTION

It has now been found that when formamidinium salts are used as the aminomethylenation reagents, simple inorganic basic compounds can be used as the base required.

The invention accordingly relates to a process for the preparation of aminomethylene compounds of the formula

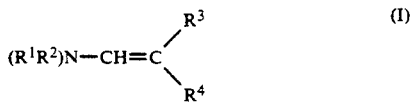

(I)

in which
R$^1$ and R$^2$ are independently of each other straight-chain or branched $C_1$-$C_8$-alkyl, $C_2$-$C_8$-alkenyl, $C_2$-$C_8$-alkoxy-alkyl, $C_3$-$C_8$-alkoxyalkenyl, $C_3$-$C_8$-cycloalkyl, $C_6$-$C_{12}$-aryl, $C_7$-$C_{10}$-aralkyl or a 5- to 8-membered saturated or unsaturated heterocyclic ring having 1 or 2 heteroatoms selected from the group comprising N, O and S, where, furthermore, R$^1$ and R$^2$, together with the N-atom on which they are substituents, can form a 5- to 8-membered saturated or unsaturated N-heterocyclic ring which can contain a further heteroatom selected from the group comprising N, O and S, and and R$^4$ are, independently of each other, $C_6$-$C_{12}$-aryl, —NO$_2$, —CN, —NC, COR$^5$, CSR$^5$, CO—OR$^5$, CO—SR$^5$ or CO—N(R$^5$,R$^6$), in which R$^5$ and R$^6$ have the range of meanings given for R$^1$ and R$^2$, but are independent of R$^1$ and R$^2$, and can additionally be hydrogen, which is characterised in that C-H-acid compounds of the formula

(II)

in which
R$^3$ and R$^4$ have the meanings given,
are reacted with salts of the formula

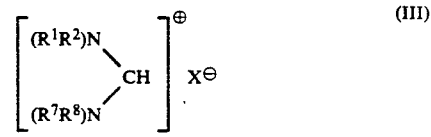

(III)

in which
R$^1$ and R$^2$ have the meanings given,
R$^7$ and R$^8$, independently of each other and independently of R$^1$ and R$^2$, have the range of meanings given for R$^1$ and R$^2$ and represent the $C_1$-$C_8$-alkylsulphate anion, the $C_6$-$C_{12}$-arylsulphonate anion, the tetrafluoroborate anion, the $C_6$-$C_{12}$-aryl sulphate anion, the chloride anion, the bromide anion, the iodide anion, the hexafluorophosphate anion, the $C_1$-$C_8$-alkylsulphonate anion, the $C_1$-$C_8$-halogenoalkylsulphonate anion, the perchlorate anion or the hexachloroantimonate anion, in the presence of a hydroxide, hydrogen carbonate or carbonate of an alkaline (earth) metal in a one-step reaction at a temperature of 10° to 70° C., preferably 20° to 60° C.

DETAILED DESCRIPTION OF THE INVENTION

Straight-chain or branched $C_1$-$C_8$-alkyl is, for example, methyl, ethyl, propyl, isopropyl, butyl, isobutyl, tert-butyl or any of the isomeric amyl, hexyl or octyl radicals, preferably the $C_1$-$C_4$-alkyl radicals mentioned.

$C_2$-$C_8$-Alkenyl is vinyl, propenyl, allyl or any of the isomeric butenyl, amylenyl, hexenyl or octenyl radicals, preferably the $C_3$-$C_4$-alkenyl radicals mentioned.

$C_2$-$C_8$-Alkoxyalkyl is for example methoxymethyl, ethoxy-methyl, methoxyethyl or other radicals selected from the group comprising $C_3$-$C_8$-alkyl in which one methylene group is replaced by an O atom.

$C_3$-$C_8$-Alkoxyalkenyl is for example methoxyvinyl, ethoxy-vinyl, methoxyallyl, 2-methoxy-propenyl or other radicals selected from the group comprising $C_4$-$C_8$-alkenyl in which a methylene group is replaced by an O atom.

$C_3$-$C_8$-Cycloalkyl is for example cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl or cyclohexyl or their methyl or dimethyl derivatives.

$C_6$-$C_{12}$-Aryl is for example phenyl, naphthyl or biphenylyl, preferably phenyl.

$C_7$-$C_{10}$-Aralkyl is for example benzyl, 1-phenyl-ethyl, 2-phenyl-ethyl or other radicals of this type known to those skilled in the art, preferably benzyl.

5- to 8-membered saturated or unsaturated heterocyclic rings having 1 or 2 heteroatoms selected from the group comprising N, O and S which may be mentioned are: pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine.

It is known to those skilled in the art that unsaturated heterocyclic rings can have a more or less highly pronounced aromatic character.

Furthermore, $R^1$ and $R^2$, together with the N-atom on which they are substituents, can form a 5- to 8-membered saturated or unsaturated (possibly aromatic) N-heterocyclic ring which can contain a further heteroatom selected from the group comprising N, O and S. Such systems are for example pyrrole, pyrrolidine, pyrroline, pyrazole, pyrazolidine, imidazole, imidazolidine, thiazole, thiazolidine, piperazine, piperidine, morpholine, azepine or dihydroazocine.

The $C_1-C_8$-alkylsulphate anion is, for example, methylsulphate, ethylsulphate, propylsulphate, isopropylsulphate, butylsulphate, isobutylsulphate, or one of the isomeric hexyl- or octylsulphates.

The $C_1-C_8$-alkylsulphonate anion or the $C_1-C_8$-halogenoalkylsulphonate anion is, for example, the anion of methylsulphonic acid, trichloromethylsulphonic acid, trifluoromethylsulphonic acid or a sulphonic acid having a higher (halogeno)alkyl radical.

The $C_6-C_{12}$-arylsulphonate anion is for example the anion of benzenesulphonic acid, naphthalene-sulphonic acid or biphenyl-sulphonic acid, preferably of benzenesulphonic acid.

The $C_6-C_{12}$-aryl sulphate anion is, for example, phenyl-sulphate, naphthylsulphate or biphenylsulphate.

$X^\ominus$ is preferably halide or alkylsulphate, particularly preferably chloride or methylsulphate.

Alkali(ne earth) metal hydroxides, hydrogen carbonates and carbonates are for example those of lithium, sodium, potassium, rubidium, caesium, magnesium, calcium, strontium or barium, preferably those of an alkali metal, particularly preferably those of sodium or potassium.

The reaction according to the invention, using NaOH as the base, for example, can be described as follows:

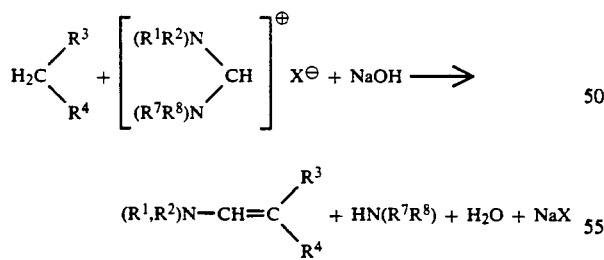

$R^7$ and $R^8$ have the range of meanings of $R^1$ and $R^2$, but are independent of $R^1$ and $R^2$. When $R^7$ and $R^8$ are different from $R^1$ and $R^2$, $R^7$ and $R^8$ radicals are chosen which enable the N atom carrying them to be eliminated as $HN(R^7R^8)$. This can be established by simple preliminary trials. Preference, however, is given to $R^7$ and $R^8$ being identical to $R^1$ and $R^2$, so that a symmetrical formamidinium salt results.

Preference is given to the use of a C-H-acid compound of the formula

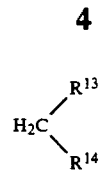

in which $R^{13}$ and $R^{14}$ are, independently of each other, phenyl, $NO_2$, CN, $COR^{15}$, $COOR^{15}$ or $CO-N(R^{15},R^{16})$, where $R^{15}$ and $R^{16}$ represent, independently of each other, hydrogen, straight-chain or branched $C_1-C_8$-alkyl, cyclopropyl, cyclopentyl, cyclohexyl, phenyl or benzyl, and where $R^{15}$ and $R^{16}$, together with the N-atom on which they are substituents, can form a 5- to 8-membered saturated or unsaturated N-heterocyclic ring which can contain a further heteroatom selected from the group comprising N, O and S.

Particular preference is given to the use of a C-H-acid compound of the formula

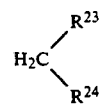

in which $R^{23}$ and $R^{24}$ are, independently of each other, phenyl, $NO_2$, CN, $COR^{25}$, $COOR^{25}$ or $CO-N(R^{25},R^{26})$, where $R^{25}$ and $R^{26}$ are, independently of each other, hydrogen or straight-chain or branched $C_1-C_4$-alkyl, and where, furthermore, $R^{25}$ and $R^{26}$, together with the N-atom on which they are substituents, can be morpholino, pyrrolidino or piperidino.

Preference is further given to reaction of the C-H-acid compounds with a salt of the formula

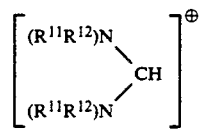

in which $R^{11}$ and $R^{12}$ are, independently of each other, straight-chain or branched $C_1-C_8$-alkyl, cyclopropyl, cyclopentyl, cyclohexyl, phenyl or benzyl, and, furthermore, $R^{11}$ and $R^{12}$, together with the N-atom on which they are substituents, can form a 5- to 8-membered saturated or unsaturated N-heterocyclic ring which can contain a further heteroatom selected from the group comprising N, O and S, and $X^\ominus$ has the range of meanings given above.

Furthermore, particular preference is given to reaction of the C-H-acid compounds with a salt of the formula

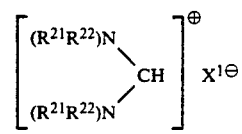

in which $R^{21}$ and $R^{22}$ are, independently of each other, straight-chain or branched $C_1$-$C_4$-alkyl, and, furthermore, $R^{21}$ and $R^{22}$, together with the N-atom on which they are substituents, can be morpholino, pyrrolidino or piperidino, and $X^{1\ominus}$ is the $C_1$-$C_8$-alkylsulphate anion, the chloride anion, the bromide anion or the iodide anion.

Great preference is given to the methyl radical as the substituents $R^{21}$ and $R^{22}$. Furthermore, very particular preference is given to $X^{1\ominus}$ being the $C_1$-$C_4$-alkyl sulphate anion, the chloride anion or the bromide anion, preferably the chloride anion or the methylsulphate anion.

Preference is given to carrying out the reaction in the presence of sodium hydroxide, sodium hydrogen carbonate or sodium carbonate or potassium hydroxide, potassium hydrogen carbonate or potassium carbonate as the base.

The C-H-acid compound, the salt and the base are generally used in a molar ratio of 1:1:1 to 1:2.5:2. Preference is given to selection of the ratio 1:1.1:1.05 to 1:1.7:1.2.

Instead of the pure formamidinium salt, the crude product of the reaction of an alkoxymethyleneiminium salt with a secondary amine may also be used, said product containing 1 equivalent of alkanol, excess amine, dialkylamine monoalkyl sulphate and dialkylformamide. In a particular embodiment, the reaction of the alkoxymethylene-iminium salt with the secondary amine, and the aminomethylenation, are carried out in one step.

The process according to the invention can in principle be carried out without solvents or diluents, since liquid materials are generally present among the starting materials or reaction products, which allows adequate mixing of the reaction mixture by means of a stirrer or a kneader. This applies in particular when the crude product of the above-mentioned reaction of an alkoxymethylene-iminium salt with a secondary amine which is used contains liquid materials.

If the salt used and the C-H-acid compound are not miscible, preference is, however, given to employment of a solvent, and to use of the resulting solution or a uniform emulsion obtained by stirring. Furthermore, it is possible to add both components (salt and C-H-acid compound) simultaneously to the base, or to introduce the salt, C-H-acid compound and base simultaneously into the reaction vessel. The addition of the salt and C-H-acid compound or of a mixture of both to the previously introduced, preferably suspended, base suppresses side reactions.

Solvents that are used are hydrocarbons such as toluene, xylene, cyclohexane or petroleum ether, halogenated hydrocarbons such as methylene chloride, alcohols, carbonyl compounds or ether, or excess secondary amine from the preliminary step. Said solvents can also be used as a mixture.

The quantity of the solvent and/or diluent is not critical for the reaction, and is, for example, 30–1000 ml, preferably 50–800 ml, particularly preferably 80–500 ml per 100 g of the reactants comprising salt, C-H-acid compound and base.

It is known to those skilled in the art, that, in such solid-liquid reactions, phase transfer catalysts (PTC) can have a reaction-accelerating effect. The process according to the invention does not need any PTC.

The base is consumed during the commencing reactions. The resulting salt precipitates out, and can easily be separated from the product dissolved in the reaction medium.

If the C-H-acid compound contains, for example, an ester group or a nitrile substituent, this is not attacked under the mild reaction conditions (for example 0.5 to 4 h and 20° to 60° C.). Even higher temperatures are possible for a short time, for example for incipient distillation.

The selectivities of the process according to the invention are very high. The conversion rates depend on the C-H-acid compound, and can attain 100%, for example in the case of esters of cyanoacetic acid at a yield of 98% of the theoretical yield. The reaction product is thus very pure, and can be used directly for further reactions.

EXAMPLE 1

A mixture of 25.1 g of 97% pure tetramethylformamidinium methylsulphate and 11.4 g of ethyl cyanoacetate was added dropwise within the course of 4 minutes to a suspension of 4.0 g of NaOH powder in 140 ml of toluene. The mixture was stirred for a further 4 h at room temperature and 1 h at 50° C., and subsequently filtered by suction at room temperature. After washing twice, each time with 10 ml of toluene, the filtrate were concentrated, and 16.8 g of product were obtained. According to gas chromatographic analysis using an internal standard, a content of 98.1% of ethyl dimethylaminomethylenecyano-acetate was established, corresponding to 98.1% of the theoretical yield.

EXAMPLE 2

The procedure of Example 1 was followed, but 0.32 g of tetrabutylammonium bromide was added at the start. 94.5% of the theoretical yield of product were obtained.

EXAMPLE 3

Analogously to Example 1, 3.3 g of 85% pure NaOH powder in 70 ml of toluene were reacted with a mixture of 14.1 g of 86.4% pure formamidinium salt and 5.7 g of cyanoacetate. 89.3% of the theoretical yield of product were obtained.

EXAMPLE 4

A mixture of 25.4 g of 86.4% pure formamidinium salt and 9.9 g of methyl cyanoacetate was added dropwise to 13.8 g of potassium carbonate in 100 ml of dried methanol. After 1 h at room temperature and 3 h at 65° C., the crystalline salt was filtered off by suction and the filtrate was concentrated. According to gas chromatographic analysis using an internal standard, 80.2% of the theoretical yield of product were present, together with 9.8% of cyanoacetate.

EXAMPLE 5

Analogously to Example 1, 3.3 g of 85% pure NaOH powder in 70 ml of methylene chloride were reacted with a mixture of 12.3 g of 86.4% pure formamidinium salt and 5.7 g of ethyl cyanoacetate. 85.0% of the theoretical yield of product were obtained, together with 6.2% of unreacted cyanoacetate.

EXAMPLE 6

5.5 g of dimethylamine were condensed with 20.9 g of methoxymethyleneiminium methylsulphate at 0° C. After stirring for 1 hour at 20° C., excess dimethylamine and 70% of the resulting methanol were removed in vacuo. Analogously to Example 1, the salt obtained was reacted with 11.4 g of ethyl cyanoacetate and 4.0 g of NaOH in 140 ml of toluene. 93% of ethyl dimethylaminomethylenecyano-acetate were obtained, together with 1.2% of the corresponding methyl ester.

EXAMPLE 7

10.6 g of sodium carbonate were added to a mixture of 13.2 g of dimethyl malonate, 23.3 g of 97% pure formamidinium salt and 50 ml of methanol at room temperature, and the mixture was subsequently refluxed for 4 h. After 50 ml of toluene had been added, the methanol was distilled off, and the salt was filtered off with suction at room temperature. The concentrated filtrate contained 40.4% of the theoretical yield of dimethyl dimethylaminomethylene-malonate and also 55.2% of unreacted malonic ester.

EXAMPLE 8

Analogously to Example 1, 25.1 g of 97% pure formamidinium salt were reacted with 13.0 g of ethyl aceto-acetate and 6.6 g of 85% pure KOH powder in 140 ml of toluene. The salt was filtered off with suction at 50° C., and the filtrate was concentrated. 66.9% of the theoretical yield of ethyl N,N-dimethylaminomethyleneaceto-acetate were obtained, together with 30.9% of acetoacetate.

EXAMPLE 9

Analogously to Example 1, 27.6 g of 95.5% pure dipyrroli-dino-formamidinium methylsulphate were reacted with 11.4 g of ethyl cyanoacetate and 4.0 g of NaOH powder in 140 ml of toluene. After work-up, 95.5% of ethyl pyrrolidino-methylenecyanoacetate were obtained.

EXAMPLE 10

4.0 g of NaOH and 8 g of pyrrolidine were introduced into 140 ml of toluene. A mixture of 20.9 g of methoxymethyleneiminium methylsulphate and 11.4 g of ethyl cyanoacetate was added dropwise at 40° C., and the reaction mixture was stirred for a further 2 h at this temperature. Mixed esters of a mixture of pyrrolidino-and dimethylaminomethylenecyanoacetic acids were obtained in 93.4% of the theoretical yield (Py:NMe$_2$=10.7:1; Et:Me=10.7:1).

EXAMPLE 11

To a suspension of 4.4 g of NaOH in 140 ml of toluene were added dropwise firstly 11.4 g of ethyl cyanoacetate and subsequently a solution of 14.6 g of 98% pure tetramethylformamidinium chloride in 25 ml of DMF. After the mixture had been stirred for 4 h at room temperature and 1 h at 50° C., the salt was filtered off with suction and the filtrate was concentrated. 92.7% of the theoretical yield of dimethylaminomethylenecyanoacetate were obtained.

What is claimed is:

1. A process for the preparation of an aminomethylene compound of the formula

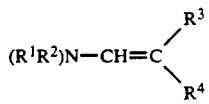

wherein

R$^1$ and R$^2$, independently of each other, represent straight-chain or branched C$_1$-C$_8$-alkyl, C$_2$-C$_8$-alkenyl, C$_2$-C$_8$-alkoxyalkyl, C$_3$-C$_8$-alkoxyalkenyl, C$_3$-C$_8$-cycloalkyl, C$_6$-C$_{12}$-aryl, C$_7$-C$_{10}$-aralkyl or a 5- to 8-membered saturated or unsaturated heterocyclic ring having 1 or 2 heteroatoms selected from the group consisting of N, O and S, or wherein R$^1$ and R$^2$, together with the N-atom to which they are attached represent a 5- to 8- membered saturated or unsaturated N-heterocyclic ring which can also contain a further heteroatom selected from the group consisting of N, O and S, and wherein R$^3$ and R$^4$, independently of each other, represent C$_6$-C$_{12}$-aryl, —NO$_2$, —CN, —NC, COR$^5$, CSR$^5$, CO—OR$^5$ CO—SR$^5$ or CO—N(R$^5$, R$^6$), in which R$^5$ and R$^6$ have the range of meanings given for R$^1$ and R$^2$, but are independent of R$^1$ and R$^2$, and can additionally represent hydrogen, wherein a C-H-acid compound of the formula

in which
R$^3$ and R$^4$ have the meanings given,
is reacted with a salt of the formula

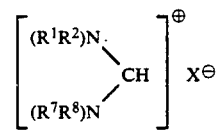

in which
R$^1$ and R$^2$ have the meanings given,
R$^7$ and R$^8$, independently of each other and independently of R$^1$ and R$^2$, have the range of meanings given for R$^1$ and R$^2$ and
X$^\ominus$ represents the C$_1$-C$_8$-alkylsulphate anion, the C$_6$-C$_{12}$-arylsulphonate anion, the tetrafluoroborate anion, the C$_6$-C$_{12}$-arylsulphate anion, the chloride anion, the bromide anion, the iodide anion, the hexafluorophosphate anion, the C$_1$-C$_8$-alkylsulphonate anion, the C$_1$-C$_8$-halogenoalkylsulphonate anion, the perchlorate anion or the hexachloroantimonate anion,
in the presence of a hydroxide, hydrogen carbonate or carbonate of an alkali(ne earth) metal in a one-step reaction at a temperature of 10° to 70° C.

2. The process of claim 1, which is carried out at a temperature of 20° to 60° C.

3. The process of claim 1, wherein a C-H-acid compound of the formula

is used, in which
R$^{13}$ and R$^{14}$, independently of each other, represent phenyl, NO$_2$, CN, COR$^{15}$, COOR$^{15}$ or CO—N(R$^{15}$, R$^{16}$), where R$^{15}$ and R$^{16}$ represent, independently of each other, hydrogen, straight-chain or branched C$_1$-C$_8$-alkyl, cyclopropyl, cyclopentyl, cyclopentyl, phenyl or benzyl, or together with the N-atom to which they are attached form a 5- to 8-membered saturated or unsaturated N-hetero-cyclic ring which can also contain a further heteroatom elected from the group comprising N, O and S.

4. The process of claim 3, wherein a C-H-acid compound of the formula

is used in which $R^{23}$ and $R^{24}$ independently of each other represent phenyl, $NO_2$, CN, $COR^{25}$, $COOR^{25}$ or $CO—N(R^{25}, R^{26})$, where $R^{25}$ and $R^{26}$ independently of each other represent hydrogen or straight-chain or branched $C_1$-$C_4$-alkyl, or together with the N-atom to which they are attached, represent morpholino, pyrrolidino or piperidino.

5. The process of claim 1, wherein a C-H-acid compound is reacted with a salt of the formula

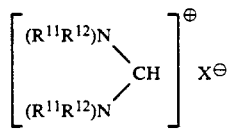

in which $R^{11}$ and $R^{12}$, independently of each other, represent straight-chain or branched $C_1$-$C_8$-alkyl, cyclopropyl, cyclopentyl, cyclohexyl, phenyl or benzyl, or together with the N-atom to which they are attached, represent a 5- to 8-membered saturated or unsaturated N-heterocyclic ring which can also contain a further heteroatom selected from the group comprising N, O and S, and $X^{\ominus}$ represents the $C_1$-$C_8$-alkylsulphate anion, the $C_6$-$C_{12}$-arylsulphonate anion, the tetrafluoroborate anion, the $C_6$-$C_{12}$-arylsulphate anion, the chloride anion, the bromide anion, the iodide anion, the hexafluorophosphate anion, the $C_1$-$C_8$-alkylsulphonate anion, the $C_1$-$C_8$-halogenoalkylsulphonate anion, the perchlorate anion or the hexachloroantimonate anion.

6. The process of claim 5, wherein the C-H-acid compound is reacted with a salt of the formula

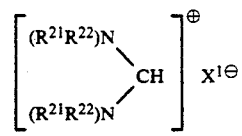

in which '$R^{21}$ and $R^{22}$ independently of each other represent straight-chain or branched $C_1$-$C_4$-alkyl, or together with the N-atom to which they are attached, represent morpholino, pyrrolidino or piperidino, and $X^{\ominus}$ represents the $C_1$-$C_8$-alkylsulphate anion, the chloride anion, the bromide anion or the iodide anion.

7. The process of claim 1, wherein the reaction is carried out in the presence of a hydroxide, hydrogen carbonate or carbonate of an alkali metal.

8. The process of claim 7, wherein the reaction is carried out in the presence of sodium hydroxide, sodium hydrogen carbonate or sodium carbonate, or potassium hydroxide, potassium hydrogen carbonate or potassium carbonate.

9. The process of claim 1, wherein the C-H-acid compound, the salt and the base are used in a molar ratio of 1:1:1 to 1:2.5:2.

10. The process of claim 9, herein the C-H-acid compound, the salt and the base are used in a molar ratio of 1:1:.1:1.05 to 1:1.7:1.2.

11. The process of claim 1, wherein the formamidinium salt is used in the form of its crude product, as obtained from the reaction of an alkoxymethyleneiminium salt with a secondary amine.

12. The process of claim 11, wherein the reaction of an alkoxymethylene-iminium salt with a secondary amine to give the formamidinium salt, and the aminomethylenation of a C-H-acid compound, are carried out in one step.

13. The process of claim 1, wherein the reaction is carried out in a solvent, and the mixture of active C-H-compound and formamidinium salt is added to a suspension of the base in the solvent.

* * * * *

UNITED STATES PATENT AND TRADEMARK OFFICE
CERTIFICATE OF CORRECTION

PATENT NO. : 5,241,099
DATED : August 31, 1993
INVENTOR(S) : Blank, et al.

It is certified that error appears in the above-indentified patent and that said Letters Patent is hereby corrected as shown below:

| | |
|---|---|
| Col. 9, line 5 | Delete " elected " and substitute -- selected -- |
| Col. 10, line 31 claim 10, line 1 | Delete " herein " and substitute -- wherein -- |
| Col. 10, line 17 | Delete " $X^{\ominus}$ " and substitute -- $X^{1\ominus}$ -- |

Signed and Sealed this

Third Day of June, 1997

Attest:

BRUCE LEHMAN

Attesting Officer

Commissioner of Patents and Trademarks